United States Patent
Aberg

(10) Patent No.: US 6,207,684 B1
(45) Date of Patent: Mar. 27, 2001

(54) COMPOUNDS WITH COMBINED ANTIHISTAMINIC AND MAST CELL STABILIZING ACTIVITIES, INTENDED FOR OPHTHALMIC USE

(75) Inventor: A. K. Gunnar Aberg, Sarasota, FL (US)

(73) Assignee: Bridge Pharma, Inc., Sarasota, FL (US)

( * ) Notice: Subject to any disclaimer, the term of this patent is extended or adjusted under 35 U.S.C. 154(b) by 0 days.

(21) Appl. No.: 09/445,118

(22) PCT Filed: Jun. 9, 1998

(86) PCT No.: PCT/US98/12031

§ 371 Date: Dec. 2, 1999

§ 102(e) Date: Dec. 2, 1999

(87) PCT Pub. No.: WO98/56381

PCT Pub. Date: Dec. 17, 1998

Related U.S. Application Data

(60) Provisional application No. 60/049,103, filed on Jun. 9, 1997.

(51) Int. Cl.[7] .................................................. A61K 31/445
(52) U.S. Cl. ............................................ 514/324; 514/912
(58) Field of Search ..................................... 514/324, 912

(56) References Cited

U.S. PATENT DOCUMENTS

| 3,749,786 | 7/1973 | Bourquin et al. | 424/267 |
| 4,073,915 | 2/1978 | Martin | 424/267 |
| 5,399,360 | 3/1995 | Surer et al. | 424/469 |

*Primary Examiner*—Zohreh Fay
(74) *Attorney, Agent, or Firm*—Nields & Lemack

(57) ABSTRACT

This invention relates to methods of treatment of ocular disease states, modulated by histaminergic and inflammatory mechanisms in a mammal using norketotifen, 10-OH-norketotifen and pharmaceutical compositions of those compounds. More particularly, this invention relates to methods of treating ocular diseases (such as, seasonal allergic conjunctivitis and other forms of conjunctivitis, keratitis, hyperemia, cellular infiltration, vascularization, fibroblastic proliferation, inflammatory cell degranulation), while avoiding certain side effects, such as local irriation, using compounds with combined antihistaminic and mast cell stabilizing activities.

7 Claims, No Drawings

COMPOUNDS WITH COMBINED ANTIHISTAMINIC AND MAST CELL STABILIZING ACTIVITIES, INTENDED FOR OPHTHALMIC USE

This application is a 371 of PCT/US98/12031 Jun. 9, 1998, which claims benefit of Provisional Application Ser. No. 60/049,103 filed Jun. 9, 1997.

BACKGROUND OF THE INVENTION

This invention relates specifically to combined antihistaminic and mast cell stabilizing compounds, having therapeutic use in various diseases, most importantly for patients suffering from ocular diseases, such as vernal conjunctivitis, keratitis, and mast cell degranulation The compound described in this invention 10-oxo-4Hbenzo[4,5]cyclohepta[1,2-b]thiophene, hereinafter called norketotifen and the 10-OH-substituted analogs thereof, hereinafter called 10-OH-norketotifen.

The parent compound of norketotifen is ketotifen, which has now been found to be less active as an antihistamine, more sedating, more toxic and more irritating to the eye than norketotifen.

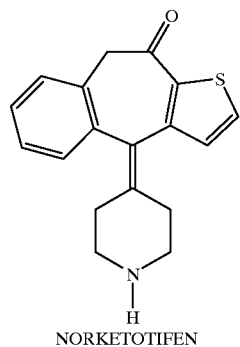

NORKETOTIFEN

Norketotifen can be metabolized in the body along various pathways. Thus, the two isomers of 10-OH norketotifen are formed by reduction of the norketotifen molecule. Norketotifen and 10-OH norketotifen can also undergo N-glucuronidation. Other metabolites, such as for example 9-OH-norketotifen and 9,10-di-OH-norketotifen may be formed and may as well be therapeutically active entities for the ocular indications of this application. The metabolic pathways are different in different species and may also be different between infants and adult humans.

SUMMARY OF THE INVENTION

Norketotifen has now been synthesized and studied pharmacologically. Surprisingly and importantly, a significant quantitative difference between ketotifen and norketotifen was found: It has now been found that norketotifen has potent anti-inflammatory and anti-histaminic effects and does not have irritating effects when applied to the eye.

It was surprisingly found that although norketotifen has more potent anti-histaminergic effects, it causes less local irritation and less sedative effects than ketotifen. It is concluded that norketotifen will have clinical utility for the treatment of various allergic and inflammatory ophthalmic conditions.

DETAILED DESCRIPTION

Pharmacological Studies of Norketotifen

As discussed above, it has now been possible to show that norketo-tifen has beneficial pharmacological effects, useful in the treatment of ophthalmic disorders, such as seasonal conjunctivitis, vernal kerato-conjunctivitis, vernal conjunctivitis, and vernal keratitis. The surprising findings are described in the following examples.

EXAMPLE 1

Binding to Histaminergic Receptors

The affinities of the test compounds for the histamine $H_1$-receptor are assessed using the [$^3$H]pyrilamine binding assay as described by Dini et al. (Agents and Actions, 1991, 33: 181–184). Briefly, membranes from guinea pig cerebellum are incubated with [$^3$H]pyrilamine and varying concentrations of the test compound(s). The specific binding of the radioactive ligand to the receptor is defined as the difference between total binding and nonspecific binding, determined in the presence of an excess of unlabelled ligand. The results are expressed as percentage of specific binding in the presence of compounds. $IC_{50}$ values (concentration required to inhibit 50% of specific binding) and Hill coefficients (nH) are determined by non linear regression analysis of the competition curves. These parameters are obtained by Hill equation curve fitting using Sigmaplot™ software.

EXAMPLE 2

Binding to Muscarinic Receptors

The experiments are carried out on membranes prepared from SF9 cells infected with bacculovirus to express human recombinant muscarinic receptor subtypes. After incubation with the test article and the proper radioligand and washing, bound radioactivity is determined with a liquid scintillation counter, using a commercial scintillation cocktail. The specific radioligand binding to each receptor is defined as the difference between total binding and nonspecific binding determined in the presence of an excess of unlabelled ligand. $IC_{50}$ values (concentrations required to inhibit 50% of specific binding) are determined by non linear regression analysis of the competition curves.

EXAMPLE 3

Studies on Sedative Effects

The physostigmine-induced lethality test used in these tests is a modification of the sedation test technique reported by COLLIER et al., in Br. J. Pharmac., 1968, 32: 295–310. In short, physostigmine (1.9 mg/kg s.c.) produces 100% lethality when given to grouped mice with 10 animals in each plastic cage (approx. 11×26×13 cm). Mice administered a sedating antihistamine prior to physostigmine are protected and survive. In the present study, test agents are administered orally 60 minutes prior to physostigmine. The number of survivors are counted 20 minutes after physostigmine administration.

Chemical Synthesis of the New Compounds

The synthesis of ketotifen, norketotifen and of (RS)-10-OH-norketotifen have been described by Waldvogel et al. (Helv Chem Acta, 1976, 59:866–877), the subject matters of which are incorporated herein by reference.

The starting compounds for these syntheses are obtained as described in Waldvogel et al.:

(1) 4-(4-piperidylidene)-9,10-dihydro-4H-benzo[4,5]-cyclohepta[1,2-b]thiophene.

(2) 4-(4-piperidylidene)-9,10-dihydro-4H-benzo[4,5]-cyclohepta[1,2-b]thiophene-10-one.

The present invention provides the active compounds norketotifen, racemic 10-OH-ketotifen, the optically active isomers of 10-OH-norketotifen, and the pharmaceutically acceptable salts and solvates thereof.

The terms "pharmaceutically acceptable salts" or "a pharmaceutically acceptable salt thereof" refer to salts prepared from pharmaceutically acceptable non-toxic acids. Suitable pharmaceutically acceptable acid addition salts for the compound of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, amndelic, methanesulfonic, mucic, nitric, pamoic, panthothenic, phosphoric, p-toluenesulfonic, succinic, sulfuric, tartaric, tromethamic and the like. The hydrogen fumarate is particularly preferred.

Pharmaceutical Compositions

The present invention also provides pharmaceutical compositions, which comprise each of the compounds norketotifen, racemic 10-OH-norketotifen, and the topically active isomers of 10-OH-norketotifen, formulated with one or more pharmaceutically acceptable carriers. The pharmaceutical compositions may be specially formulated for oral, conjunctival, sublingual, parenteral, transdermal, rectal, buccal, topical or nasal administration or for administration by inhalation of powder or aerosol.

The pharmaceutical compositions of this invention can be administered to humans and other mammals by various routes of administration, for example, by oral, conjunctival, sublingual, buccal, parenteral, cutaneous, transdermal, rectal, topical, or nasal administration, or as an oral or nasal spray or aerosol. The term "parenteral" refers to but is not limited to intravenous, intraarterial, intramuscular, intraperitoneal, intracutaneous, subcutaneous, retrobulbar and intraarticular administration. The term "transdermal" includes to but is not limited to administration by use of various devices ("patches" etc.) that facilitate or control the transport or absorption of the drug through tissues.

Oral Administration Forms

Pharmaceutical compositions of this invention for oral administration of solid dosage forms, include tablets, capsules, pills, granules, and powders. In such solid dosage forms, the active compound may be mixed with one or more pharmaceutically acceptable excipients or carriers (ex. sodium citrate, dicalcium phosphate), fillers or extenders (ex. starch, lactose, sucrose, glucose, mannitol, silicic acid), binders (ex. carboxymethyl-cellulose, alginates, gelatin, polyvinylpyrrolidone, sucrose, acacia), humectants (ex. glycerol), disintegrating agents (ex. agar-agar, calcium carbonate, starch alginic acid, silicates, sodium carbonate), solution retarding agents (ex. paraffin), absorption accelerators (ex. quarternary ammonium compounds), wetting agents (ex. cetyl alcohol, glycerol monostearate), absorbents (ex. kaolin, bentonite clay), lubricating agents (ex. talk, calcium stearate, magnesium stearate, polyethylene glycols, sodium lauryl sulfate), and/or buffering agents. Regular tablets can be composed according to Example 4.

EXAMPLE 4

Tablet Formulations

| Ingredients | per tablet | per batch of 10,000 tablets |
|---|---|---|
| Norketotifen | 2 mg | 20 g |
| Microcrystalline cellulose | 30 mg | 300 g |
| Lactose | 70 mg | 700 g |
| Calcium stearate | 2 mg | 20 g |
| FD&C Blue #1 Lake | 0.03 mg | 300 mg |

The active ingredient (norketotifen) in this example is blended with the lactose and cellulose until a uniform blend is formed. The lake is added and further blended. Finally, the calcium stearate is blended in, and the resulting mixture is compressed into tablets using a 9/32 inch (7 mm) shallow concave punch. Tablets of other strengths may be prepared by altering the ratio of active ingredient to the excipients or to the final weight of the tablet.

Solid forms of capsules, dragees, granules, pills, and tablets can have coatings and/or shells (ex. enteric coatings) known in the pharmaceutical formulating art. The compositions may also be designed to release the active ingredient (s) in a certain part of the gastrointestinal tract or in a controlled release, slow-release or in a delayed-release manner.

The active compound(s) can also be micro-encapsulated with one or more of the above-mentioned excipients.

Liquid dosage forms for oral administration include pharmaceutically acceptable emulsions, solutions, suspensions, syrups and elixirs. The liquid dosage form may also contain commonly known diluents (ex. water, other solvents, solubilizing agents), emulsifiers (ethanol, isopropyl alcohol, ethyl carbonate, ethyl acetate, benzyl alcohol, benzyl benzoate, propylene glycol, butylene glycole, dimethyl formamide, oils, oleic acid, glycerol, tetrahydrofurfuryl alcohol, polyethylene glycols, sorbitan fatty esters, and mixtures thereof.

Suspensions may contain one ore more suspending agents known in the pharmaceutical formulating art.

Oral compositions may also be designed for lymphatic absorption of the active ingredient(s), using for example oleic acid to activate lymphatic absorption from the gastrointestinal tract.

Topical Administration Forms (Including Forms for Conjunctival Instillation)

Compositions for topical administration of the compounds of this invention include solutions, suspensions, droplets, sprays, ointments and powders.

In addition to the therapeutically active ingredients, the composition of this invention for topical ocular or conjunctival administration may further comprise various formulatory ingredients, such as antimicrobial preservatives and tonicity agents. Examples of suitable antimicrobial preservatives include: benzalkonium chloride, thimerosal, chlorobutanol, methyl paraben, propyl paraben, phenylethyl alcohol, edetate disodium, sorbic acid, ONAMER M and other agents, known to those skilled in the art. Such preservatives, if utilized, will typically be employed in an amount from 0.001% to 1.0% by weight (wt. %). Examples of suitable agents which may be utilized to adjust the tonicity or osmolality of the formulations include sodium chloride, potassium chloride, mannitol, dextrose glycerine and propylene glycol. Such agents, if utilized, will be employed in an amount of 0.1% to 10.0% by weight (wt. %). Various penetration-enhancing agents, such as for example DMSO, DMAC and hydroxypolyethoxydodecane may also be included. The compositions are preferably aqueous, and have a pH in the range of 3.5 to 8.0.

As will be appreciated by those skilled in the art, the compositions may be formulated in various dosage forms suitable for topical ophthalmic delivery, including solids, solutions, suspensions, emulsions, gels, and erodible solid ocular inserts.

Parenteral Administration Forms

Pharmaceutical compositions for parenteral injections include pharmaceutically acceptable sterile aquous or nonaquous solutions, dispersions, suspensions, emulsions and sterile powders for reconstitution into sterile injectable solutions or dispersions prior to use. Various aquous and nonaquous carriers, diluents solvents and vehicles may be used (ex. water, ethanol, glycerol, glycol), as well as vegetable oils (ex. olive oil), and organic esters (ex ethyl oleate), or mixtures thereof may be used. Fluidity can be maintained by use of coating material such as lecithin, by restricting particle size and by use of surfactants.

The compositions may also contain adjuvants such as preservatives, wetting agents, emulsifying agents, dispersing agents, antibacterial agents, antifungal agents, isotonic agents, and/or absorption-delaying agents. Absorption-prolonging or absorption-delaying delaying effects may be achieved by injecting a crystalline or amorphous suspension with low water solubility. Delayed absorption may also be obtained by dissolving or suspending the drug in an oil vehicle or by using injectable depot forms (ex. microencapsulated matrices of the drug in biodegradable polymers, such as polyanhydrides, polylactide-polyglycolide, polyorthoesters) or by using various types of liposomes or microemulsions to hold the drug. Formulations for injection can be sterilized by various methods.

Topical and transdermal delivery forms are here also embodied as parenteral administration forms.

Oral or Nasal Spray or Droplet Administration

Compositions for oral or nasal sprays or droplets may be in the form of solutions, suspensions or dry powders and may be designed for nasal, buccal, bronchial/pulmonary, and/or gastric absorption of the drug.

Buccal Administration Forms

Compositions for buccal administration are preferably toothpastes, mouthwashes, sublingual preparations, chewing gums, etc.

Transdermal Administration Forms

Compositions for transdermal administration of the compounds of this invention include various transdermal delivery systems, such as for example patches, bandages etc. Various penetration-enhancing agents, such as for example DMSO, DMAC and hydroxypolyethoxydodecane may also be included.

Rectal Administration Forms

Compositions for rectal administration are preferably suppositories.

Therapeutic Dose Levels

The actual dosage levels of active ingredients in the pharmaceutical compositions of this inventions may be varied so as to obtain the desired therapeutic effect. Thus the amount of drug used varies and may depend on factors such as administration form, severity of the disease, frequency of dosing etc. As an example, for use as medication to patients suffering from allergic conjunctivitis oral doses of the compounds of this invention are used at dose levels of 0.1 mg to about 100 mg, preferably from 0.2 mg to 10 mg once to four times daily to a patient weighing 60 kg. For patients suffering from seasonal conjunctivitis, the concentration of the compounds of this invention in solutions or gels for instillation into the conjunctival sac range from 0.01% to 5.0%, preferably 0.02% to 1.0%. The frequency and amount of the dosage will be determined by the clinician based on various clinical factors, such as for example the weight and the severity of the disease of the patient. The use will typically comprise topical application of one to two drops (or an amount of a solid or semisolid dosage form) to the affected eye one to four times per day.

This invention provides methods for treatment and/or prophylaxis of all forms of ocular and conjunctival allergic, immunological and inflammatory disorders in mammals, such as humans, while avoiding ocular irritation, sedation and other toxic manifestations of ketotifen. These methods comprise administering to the mammal in need of such treatment and/or prophylaxis, effective amounts of norketotifen or 10-OH-norketotifen or pharmaceutically acceptable salts thereof.

This invention also provides methods for co-administration of norketotifen or 10-OH-norketotifen or an optically active isomer of thereof with at least one drug of the following classes: ocular antihypertensive agents, adrenergic agonists or antagonists, antibacterial agents, antiviral agents, steroids, cyclooxygenase inhibitors, leukotriene antagonists, lipoxygenase inhibitors and other ocular therapeutic remedies. In particular, the present invention provides for co-administration of norketotifen or of 10-OH-norketotifen or an isomer thereof with an ophthalmic decongestant, such as for example phenylephedrine, naphazoline or tetrahydrozoline.

The invention also provides methods for administration of norketotifen or 10-OH-norketotifen or an optically active isomer of thereof in conjuction with surgical procedures to minimize inflammation or irritation and improve the post-surgical healing process.

Equivalents

The person skilled in the art of pharmacology will realize that the conditions to be treated according to this invention are those, caused by the release of mediators such as histamine, platelet aggregating factor, leukotrienes, thromboxanes and other arachidonate products and cytokines, being released form inflammatory cells such as for example mast cells, eosinophils, leucocytes etc, the granulation of such cells being inhibited by a "mast cell stabilizer", and those caused by histamine binding to histamine receptors, which can be inhibited by a histamine receptor blocker and those caused by both inflammatory cell degranulation and by histamine-induced activation of target cells, tissues and organs.

The person skilled in the art will realize that by using a single isomer (eutomer) of 10-OH-norketotifen in stead of racemic 10-OH-norketotifen, it is possible to avoid the side effects residing in the other isomer (distomer).

What is claimed is:

1. A method for preventing or treating ophthalmic disorders, which comprises administering to a mammal in need of such treatment a therapeutically effective amount of a composition comprising a compound selected from the group consisting of norketotifen and 10-OH-norketotifen or a pharmaceutically acceptable salt thereof, together with a pharmaceutically acceptable carrier.

2. The method of claim 1, wherein said ophthalmic disorder is selected from the group consisting of allergic condition, an immunologic condition, and an inflammatory condition.

3. The method of claim 2, wherein said ophthalmic disorder is selected from the group consisting of seasonal allergic conjunctivitis, vernal keratoconjunctivitis, vernal conjunctivitis, and vernal keratitis.

4. The method of claim 1, wherein from about 0.01 to 100 mg is administered from one to four times daily.

5. The method of claim 4, wherein the concentration of said compound in said composition is from about 0.01 to 2 percent.

6. The method of claim 1, wherein said composition further comprises an ophthalmic decongestant.

7. A topical ophthalmic composition comprising a therapeutically effective amount of a compound selected from the group consisting of norketotifen and 10-OH-norketotifen or a pharmaceutically acceptable salt thereof, together with a pharmaceutically acceptable topical carrier.

* * * * *